(12) United States Patent
Campbell et al.

(10) Patent No.: US 9,677,987 B2
(45) Date of Patent: Jun. 13, 2017

(54) MEASUREMENT OF PARTICULATE MATTER DELIQUESCENCE RELATIVE HUMIDITY

(71) Applicant: International Business Machines Corporation, Armonk, NY (US)

(72) Inventors: Levi A. Campbell, Poughkeepsie, NY (US); Prabjit Singh, Poughkeepsie, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/017,689

(22) Filed: Feb. 8, 2016

(65) Prior Publication Data

US 2017/0023460 A1 Jan. 26, 2017

Related U.S. Application Data

(63) Continuation of application No. 14/805,502, filed on Jul. 22, 2015.

(51) Int. Cl.
*G01N 27/12* (2006.01)
*G01N 15/06* (2006.01)

(52) U.S. Cl.
CPC ....... *G01N 15/0656* (2013.01); *G01N 27/121* (2013.01)

(58) Field of Classification Search
CPC .......................... G01N 15/0656; G01N 27/121
USPC ...................... 73/29.01, 29.05, 335.05, 28.01
See application file for complete search history.

(56) References Cited

U.S. PATENT DOCUMENTS

| | | | | |
|---|---|---|---|---|
| 4,473,813 A | * | 9/1984 | Kinjo | G01N 27/121 338/35 |
| 4,642,601 A | * | 2/1987 | Sugawara | G01N 27/121 338/34 |
| 5,246,023 A | | 9/1993 | Breunsbach et al. | |
| 5,247,827 A | | 9/1993 | Shah | |
| 6,834,547 B2 | * | 12/2004 | Chen | G01N 27/121 73/29.05 |
| 8,402,813 B2 | | 3/2013 | Kruse et al. | |
| 8,578,756 B2 | | 11/2013 | Suzuki | |
| 8,640,526 B2 | | 2/2014 | Di Miro et al. | |

(Continued)

FOREIGN PATENT DOCUMENTS

CN 101226159 A 7/2008
DE 102013103127 * 5/2014

OTHER PUBLICATIONS

Yang et al., "Deliquescence Relative Humidity Measurements Using an Electrical Conductivity Method", Journal of Solution Chemistry, vol. 35, No. 4, Apr. 2006, pp. 583-604.

(Continued)

*Primary Examiner* — Daniel S Larkin
(74) *Attorney, Agent, or Firm* — L. Jeffrey Kelly

(57) ABSTRACT

A method includes measuring a leakage current through a particulate matter sample in a humidity chamber, the leakage current is measured as a relative humidity in the humidity chamber is incrementally increased, and plotting a logarithm of the measured leakage current as a function of the relative humidity. The plot of the logarithm of the measured leakage current as a function of the relative humidity has an inversion region, a low relative humidity region, and a high relative humidity region.

1 Claim, 9 Drawing Sheets

(56) References Cited

U.S. PATENT DOCUMENTS

| | | |
|---|---|---|
| 8,683,861 B2 | 4/2014 | Humbert et al. |
| 8,707,761 B2 | 4/2014 | Maeda et al. |
| 8,950,239 B2 | 2/2015 | Kuczynski et al. |
| 2003/0029232 A1 | 2/2003 | Felix et al. |
| 2010/0206043 A1* | 8/2010 | Tewarson .................. G01N 1/26 73/23.41 |
| 2015/0293046 A1* | 10/2015 | Klein ................... G01N 27/048 73/335.05 |

OTHER PUBLICATIONS

Grace Period Disclosure, Singh et al., "Characterization, Prevention and Removal of Particulate Matter on Printed Circuit Boards", Proceedings of the IPC APEX Conference, pp. 1-10.

"2011 Gaseous and Particulate Contamination Guidelines For Data Centers1", 2011, American Society of Heating, Refrigerating and Air-Conditioning Engineers, Inc., pp. 1-22.

* cited by examiner

MEASUREMENT OF PARTICULATE MATTER DELIQUESCENCE RELATIVE HUMIDITY

RELATED APPLICATIONS

This application is a continuation of co-pending U.S. application Ser. No. 14/805,502, filed 22 Jul. 2015.

BACKGROUND

The present invention generally relates to the field of particulate matter contamination in electronic packaging for computer systems, and more particularly to measuring the deliquescence relative humidity of dust.

The physical environment surrounding a printed circuit board (PCB) is defined by the temperature, humidity and gaseous and particulate contamination in the air. Environmental factors may cause PCBs to fail in two ways: First, electrical open circuits may result from corrosion, such as the corrosion of silver terminations in surface mount components. Second, electrical short circuits may be caused by (a) copper creep corrosion, (b) electrochemical reactions such as ion migration and cathodic-anodic filamentation or (c) settled, hygroscopic particulate matter contamination reducing the surface insulation resistance between closely spaced features on PCBs. In 2006, the European Union's Restriction of Hazardous Substances (RoHS) directive banning the use of lead in solders led to changes in PCB finishes and the elimination of lead from solders. These changes dramatically increased the PCB failure rates due to creep corrosion. Another common failure mode during this period was that of surface mount resistors suffering open circuits due to the corrosion of their silver terminations. Information technology (IT) equipment manufacturers have since learned to make their hardware robust against these two failure modes, which used to occur predominantly in geographies with high levels of sulfur-bearing gaseous contamination. The failure mode that is much more difficult to deal with and eliminate is that of the electrical short circuiting caused by the accumulated particulate matter in humid environments. The difficulty arises from the intermittent electrical nature of these particles and that the failure leaves no visible evidence besides the presence of deposited particulate matter.

The rapid expansion of the IT equipment market in the polluted geographies of Asia that have high levels of fine particulate matter in the ambient air and the increasing use of free cooling is introducing this new, often intermittent, short-circuit failure mode due to particulate matter. The source of particulate matter is both natural and anthropogenic. In terms of size, particulate matter may be divided into two categories: fine and coarse particles. Fine particles (<2.5 μm), such as those found in motor vehicle exhaust, diesel particulate matter (DPM), smoke and haze, are of two types: primary and secondary. The primary fine particles are directly emitted from a source, such as a forest fire, volcanoes, construction sites, unpaved roads, fields or smokestacks. The secondary fine particles, which make up most of the fine particulate pollution, are those formed as a result of photochemical reactions in the atmosphere. This is generally due to the presence of oxides of nitrogen and sulfur emitted from power plants, industries and automobiles. Sulfur dioxide and nitrogen dioxide interact with <0.1 μm size carbonaceous material seed particles in a complex, multistep photochemical process to produce sulfuric and nitric acids. These acids are neutralized by ammonia from fertilizers, decay of biological materials and other sources to produce fine particles dominated by ammonium sulfate, ammonium hydrogen sulfate and ammonium nitrate. The majority of these secondary fine particles would be considered anthropogenic. Coarse particles, which are in the 2.5-15 μm size range, include sea salt, natural and artificial fibers, plant pollens, and wind-blown dust. Their sources include erosion of soil and minerals and flaking of biological materials.

SUMMARY

According to an embodiment of the present disclosure, a method may include measuring a leakage current through a particulate matter sample in a humidity chamber, the leakage current is measured as a relative humidity in the humidity chamber is incrementally increased, and plotting a logarithm of the measured leakage current as a function of the relative humidity, the plot of the logarithm of the measured leakage current as a function of the relative humidity has an inversion region, a low relative humidity region, and a high relative humidity region.

According to another embodiment of the present disclosure, a method may include placing an interdigitated comb coupon including a plurality of interdigitated combs in a data center for a period of time sufficient for particulate matter to settle on the interdigitated comb coupon, placing the interdigitated comb coupon with the particulate matter within a humidity chamber, measuring a leakage current through the particulate matter bridging the plurality of interdigitated combs, the leakage current is measured as a relative humidity in the humidity chamber is incrementally increased, and plotting a logarithm of the measured leakage current as a function of the relative humidity, the plot of the logarithm of the measured leakage current as a function of the relative humidity has an inversion region, a low relative humidity region, and a high relative humidity region.

According to another embodiment of the present disclosure, a method may include providing a printed circuit board contaminated with particulate matter, washing the contaminated printed circuit board with a deionized water and isopropyl alcohol solution, collecting the deionized water and isopropyl alcohol solution containing the particulate matter, concentrating the deionized water and isopropyl alcohol solution by evaporation, dispensing the concentrated deionized water and isopropyl alcohol solution on an interdigitated comb coupon having a plurality of interdigitated combs, allowing the concentrated deionized water and isopropyl alcohol solution on the interdigitated comb coupon to dry, placing the interdigitated comb coupon including the particulate matter within a humidity chamber, measuring a leakage current through the particulate matter bridging the plurality of interdigitated combs, the leakage current is measured as a relative humidity in the humidity chamber is incrementally increased, and plotting a logarithm of the measured leakage current as a function of the relative humidity, the plot of the logarithm of the measured leakage current as a function of the relative humidity has an inversion region, a low relative humidity region, and a high relative humidity region.

BRIEF DESCRIPTION OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

Embodiments of the present invention generally relate to the field of particulate matter contamination in electronic packaging for computer systems, and more particularly to measuring the deliquescence relative humidity of dust.

Particle contamination that has accumulated on printed circuit boards (PCBs) may cause electrical short-circuit failures mainly because particulate matter's electrical resistance decreases sharply when the relative humidity of the surrounding air increases above the deliquescence relative humidity (DRH) of the particulate matter. The corrosion behavior of particulate matter is best characterized by its DRH, which is the relative humidity of the air at which the particulate matter absorbs enough moisture from the air to dissolve in the absorbed water and form an ionically conductive solution.

By developing a method to determine the deliquescence relative humidity of particulate matter suitable for failure analysis of electronic hardware, embodiments of the present disclosure may, among other potential benefits, provide a method to test 1 mg or less of available particulate matter, so as to help prevent particulate contamination from entering the data center and settling on information technology (IT) equipment, and provide a way to clean contaminated equipment. As such, the present embodiments may reduce failures associated with particulate matter contamination in IT equipment.

Figure 1:
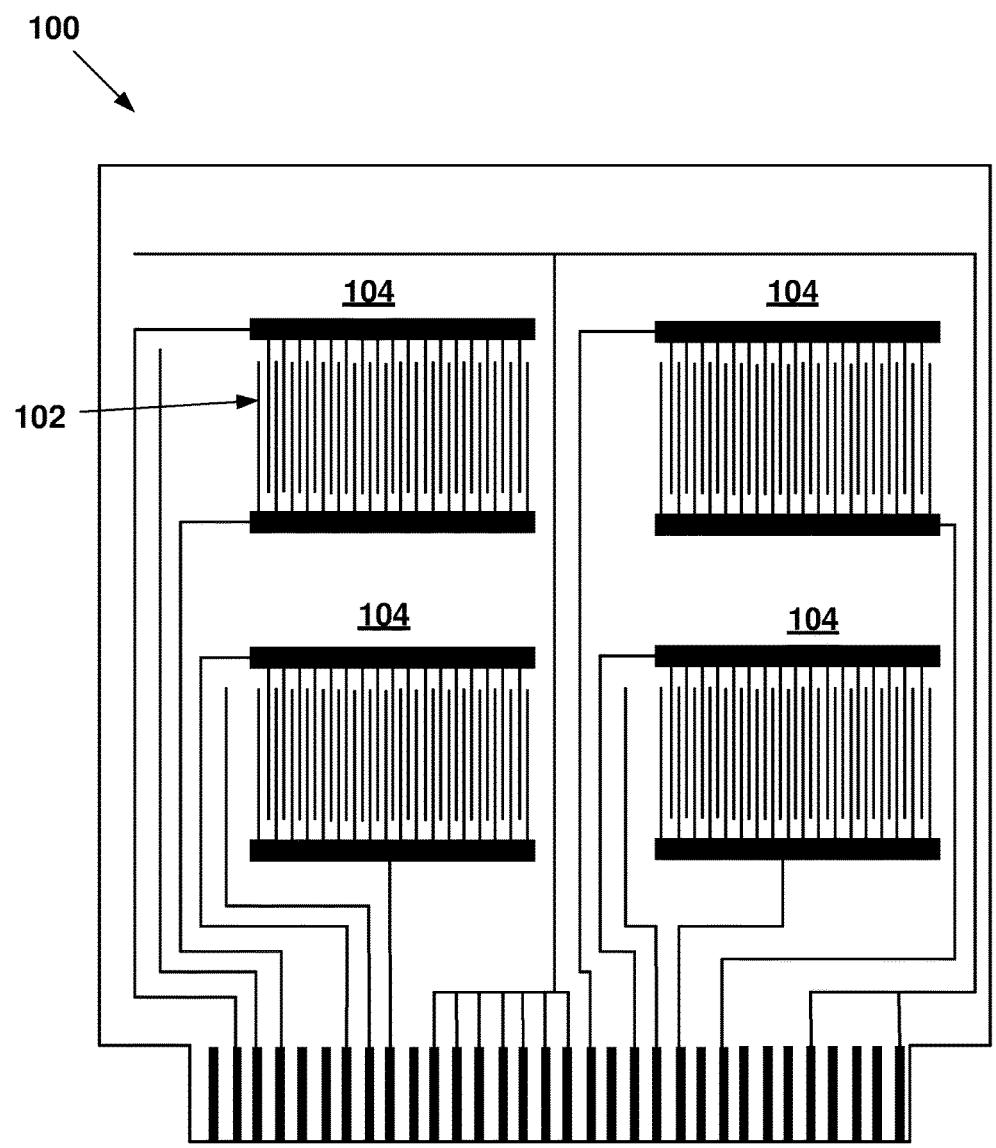
FIG. 1 depicts a top view of an interdigitated comb pattern coupon, according to an embodiment of the present disclosure.

Referring to FIG. 1, an exemplary interdigitated comb pattern coupon 100 (also referred to as interdigitated comb coupon) is shown, according to an embodiment of the present disclosure. In this embodiment, the interdigitated comb coupon 100 may include industry standard test boards IPC-B-24 Rev A. The interdigitated comb coupon 100 may include a plurality of interdigitated combs 102 (hereinafter interdigitated combs) separated by a gap (not shown) of approximately 0.5 mm which the particulate matter has to bridge to conduct current between the interdigitated combs 102.

The interdigitated comb coupon 100 (test board) may typically include four independent comb pattern areas (also referred to as comb patterns) 104 as illustrated in FIG. 1, allowing four particulate matter specimens to be tested simultaneously. In embodiments in which the amount of particulate matter available for analysis is limited to less than a milligram, the available analysis options may be limited to electrical and gravimetric methods. Since IT equipment reliability may be directly influenced by changes in the electrical conductivity of the wetted particulate matter, embodiments of the present disclosure focus on developing an electrical method for measuring DRH of particulate matter (e.g. dust). It should be noted that gravimetric tests were also conducted to interpret and support the electrical conductivity test results.

The electrical conductivity test method of measuring the DRH of particulate matter may start by dispensing the particulate matter under test onto the interdigitated comb coupon 100. Then, a voltage may be applied across the interdigitated combs 102, and the leakage current through the particulate matter bridging the interdigitated combs 102 may be measured and plotted as a function of relative humidity. The DRH may be obtained from the plot of leakage current versus relative humidity as will be described in detail below.

In order to perform the described measurements, a sample of the particular matter (dust) may be collected and dispensed on the combs pattern areas 104 of the interdigitated comb coupon 100. In one embodiment, a soft brush may be used to sweep the dust into a clean plastic bag to transport to an analysis laboratory. It should be noted that, in this embodiment, it may be difficult to sweep the fine dust off the surface into the plastic bag and that once the dust is in the bag, it may be difficult to sprinkle the dust onto the combs pattern areas 104 in a controlled manner.

In another embodiment, one or more witness interdigitated comb test boards, such as the interdigitated comb coupon 100, may be placed in the data center under study for a period of time (e.g., one month), to allow sufficient time for dust particles to settle on the test board. Then, the contaminated test boards may be returned to a laboratory for DRH measurement.

In yet another embodiment, a contaminated PCB may be shipped to a laboratory where it may be washed with a deionized water and isopropyl alcohol solution. The wash liquid containing the particulate matter may be collected and concentrated by evaporation. Then concentrated drops, preferably 10 drops, each 10 µl in volume, may be dispensed on the combs pattern areas 104 and dried. It should be noted that this may be the most convenient method of collecting particulate matter accumulated on PCBs.

In the laboratory, the interdigitated comb coupon 100 with a uniform covering of particulate matter obtained by any of the methods previously described, may be placed in a precision humidity chamber at a constant temperature of interest, generally in the 25-30° C. range. The starting relative humidity in the chamber should be at the lower limit of the chamber capability. The relative humidity is raised in 10% steps and the leakage current through the particulate matter, at a predetermined set voltage, measured and plotted versus relative humidity as will be described in detail below. The deliquescence relative humidity has previously been derived from these leakage current vs. relative humidity plots as the relative humidity at which there is a sudden rise in the electrical conductivity of the particulate matter.

As may be known to those skilled in the art, it is a standard practice to measure conductivity of the particulate matter by applying a constant voltage, typically 10 Vdc, across the interdigitated combs and measuring the leakage current through the particulate matter. However, experimental results have shown that each time the relative humidity stepped up, there was a sudden rise in leakage current followed by a decay of the current. Also, relative humidity stepping up from approximately 75% to approximately 83% caused a drop in the leakage current instead of the expected rise. These observations may be explained on the basis that continuous application of 10 Vdc across the combs may cause electrochemical reactions in the inter-comb space that may deplete the mobile ions and cause enough gas evolution to form vapor which is not electrically conductive.

Figure 2A:
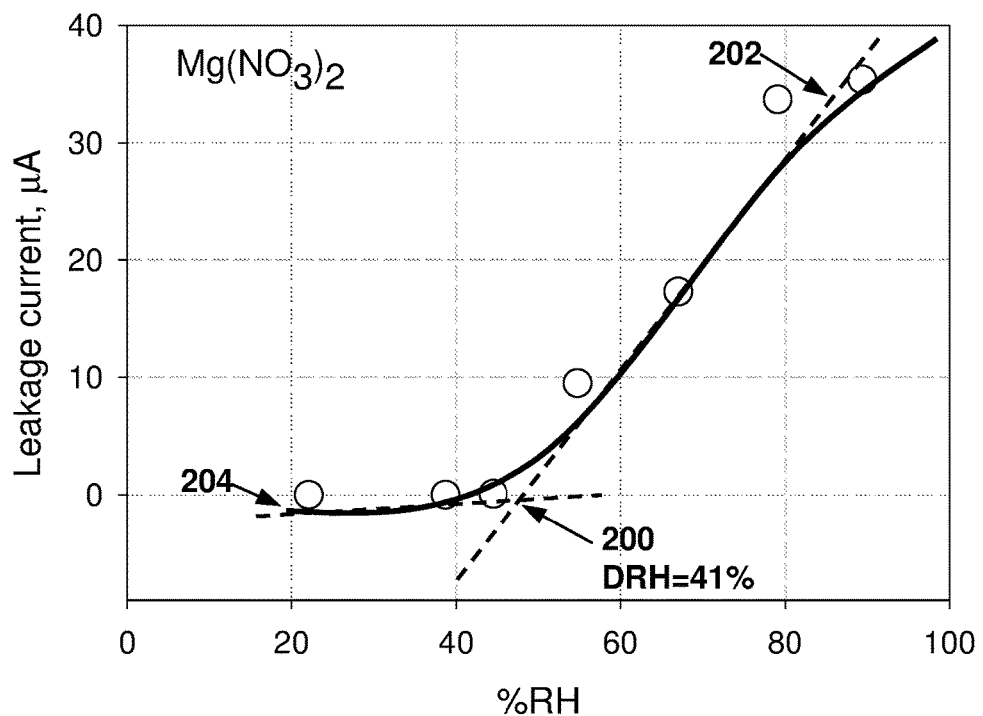
FIGS. 2A-2C depicts plots of leakage current vs. percent relative humidity for different salts on a silver-plated interdigitated comb pattern at 25° C. using a linear scale, according to an embodiment of the present disclosure.
Figure 2B:
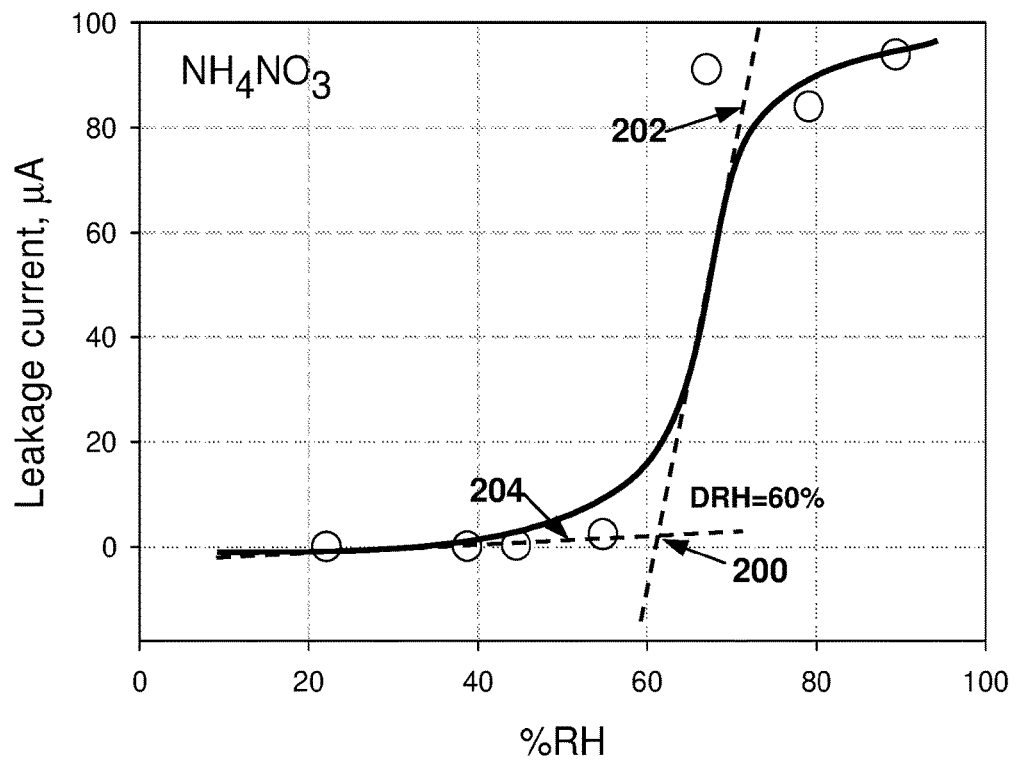
Figure 2C:
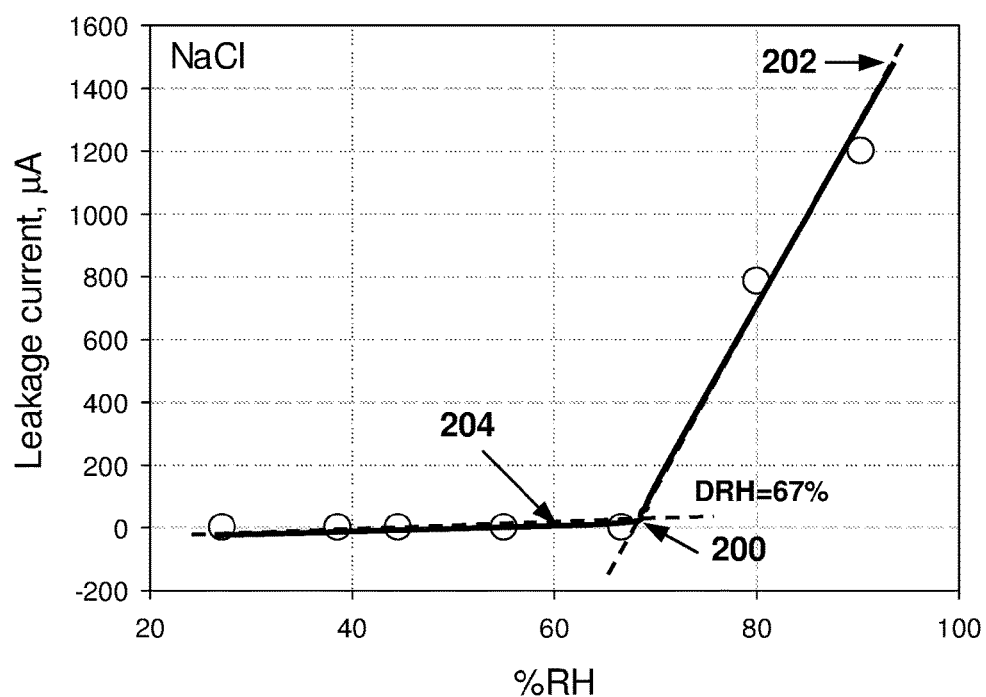

Referring now to FIGS. 2A-2C, leakage current vs. percent (%) relative humidity (RH) plots of different salts on a silver-plated interdigitated comb pattern at 25° C. using a linear scale are shown, according to an embodiment of the present disclosure. The procedure to determine the DRH of the collected particulate matter samples may start by using a potentiostat to measure the leakage current through the particulate matter bridging the interdigitated combs 102 (FIG. 1) by applying a square waveform voltage across the interdigitated combs 102 (FIG. 1).

In this embodiment, the potentiostat was capable of measuring current in the low nano-ampere range with substantial accuracy. The applied voltage was limited to two cycles lasting a total of 4 seconds to minimally disturb the electrochemistry of the particulate matter being tested. As a first step in the test development, three salts including magnesium nitrate [$Mg(NO_3)_2$], ammonium nitrate [$NH_4NO_3$] and sodium chloride [NaCl], with published DRH values at 25° C. of 53%, 62% and 75%, respectively, were studied. Ten drops, each 10 µl in volume, of a 0.1 wt % salt solution were dispensed onto each comb pattern and dried. The comb coupons, including the interdigitated comb coupon 100, were placed in a temperature-humidity chamber and the humidity set at the lowest value the chamber could achieve, which may be approximately 30%.

Next, the relative humidity was raised in steps of roughly 10% and the time at each percent relative humidity (% RH) step was approximately one hour. Leakage current was measured at the end of each % RH step and plotted versus percent relative humidity for each salt as shown in FIGS. 2A-2C and 3A-3C.

It should be noted that when plotting the leakage current versus percent relative humidity using a liner scale as shown in FIGS. 2A-2C, interpreting the linear plots in terms of an intercept 200 between a low humidity asymptote 204 and a high humidity asymptote 202 being the deliquescent relative humidity of the salts may not be accurate. More specifically, the intercept 200 does not coincide with the published values of the DRH of the studied salts ($Mg(NO_3)_2$, $NH_4NO_3$ and NaCl), since they may depend on the magnitude of the vertical scale. Therefore, in order to determine the DRH values that may agree with the published values for $Mg(NO_3)_2$, $NH_4NO_3$ and NaCl the logarithm of the leakage currents for the three salts are plotted versus percent relative humidity as illustrated in FIGS. 3A-3C.

Figure 3A:
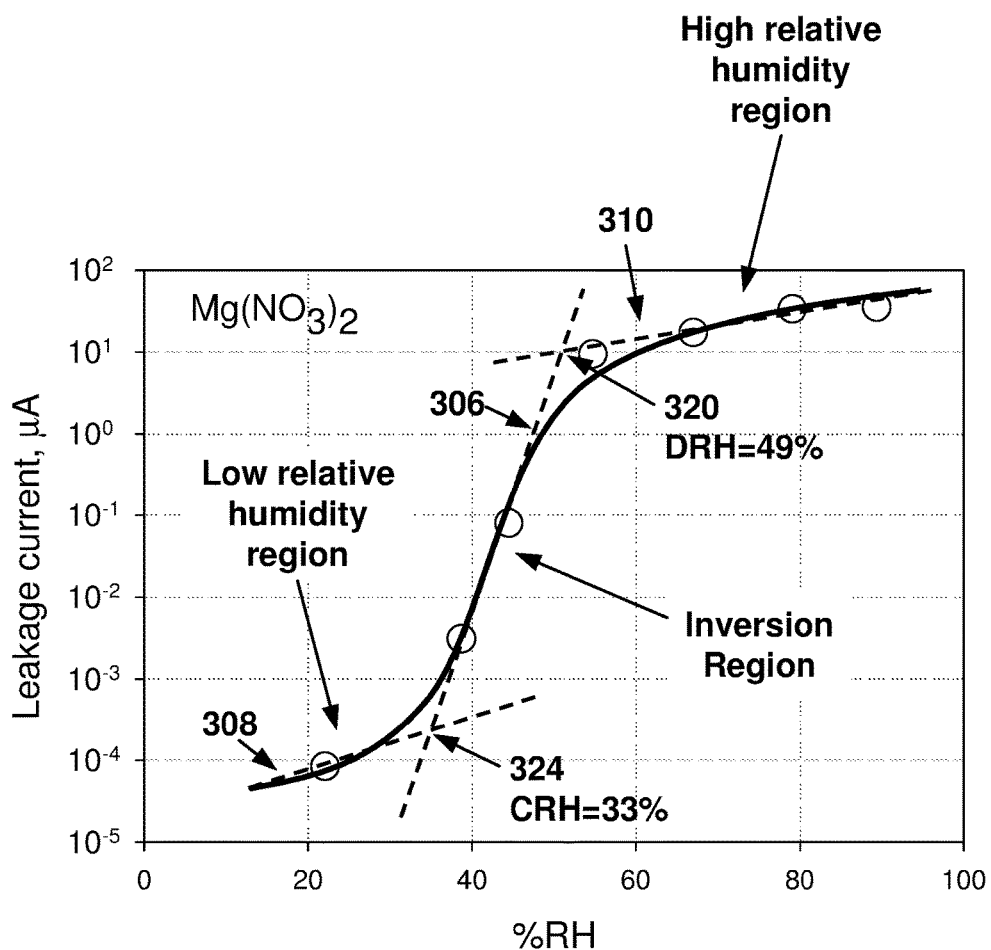
FIGS. 3A-3C depicts plots of leakage current vs. percent relative humidity for different salts on a silver-plated interdigitated comb pattern at 25° C. using a logarithmic scale, according to an embodiment of the present disclosure.
Figure 3B:
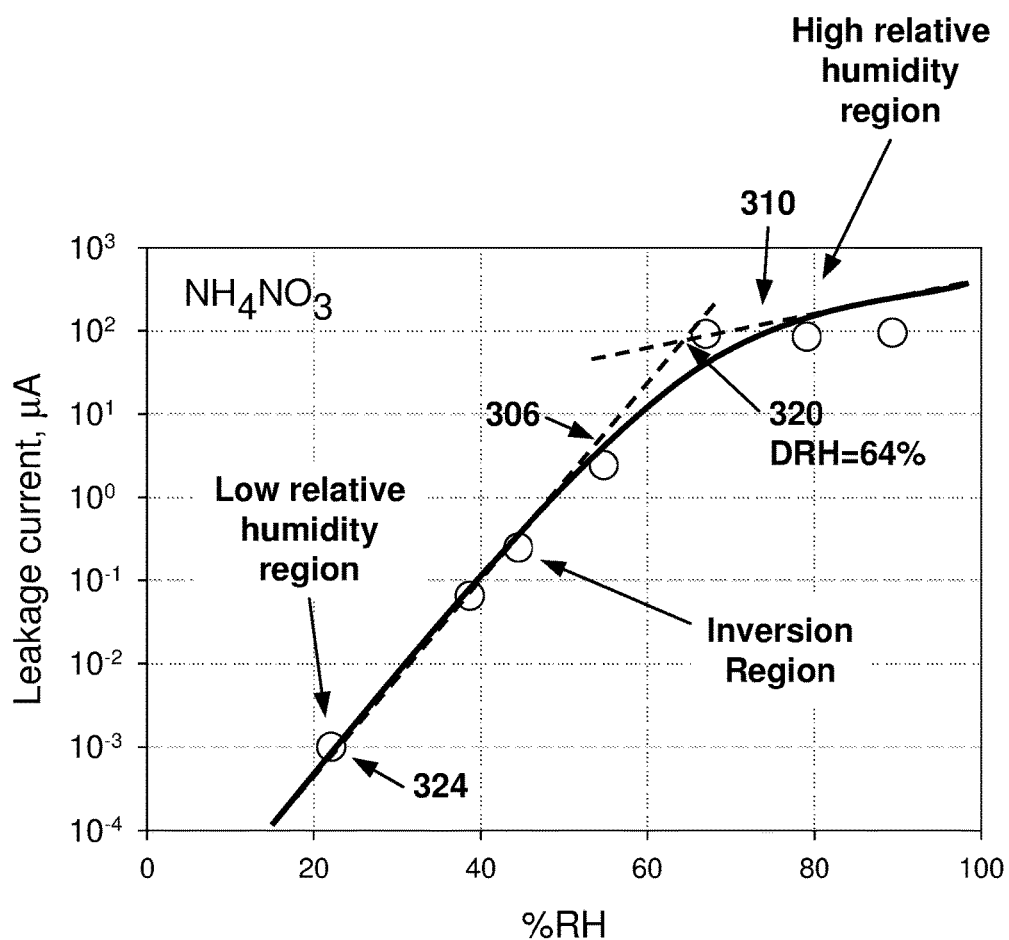
Figure 3C:
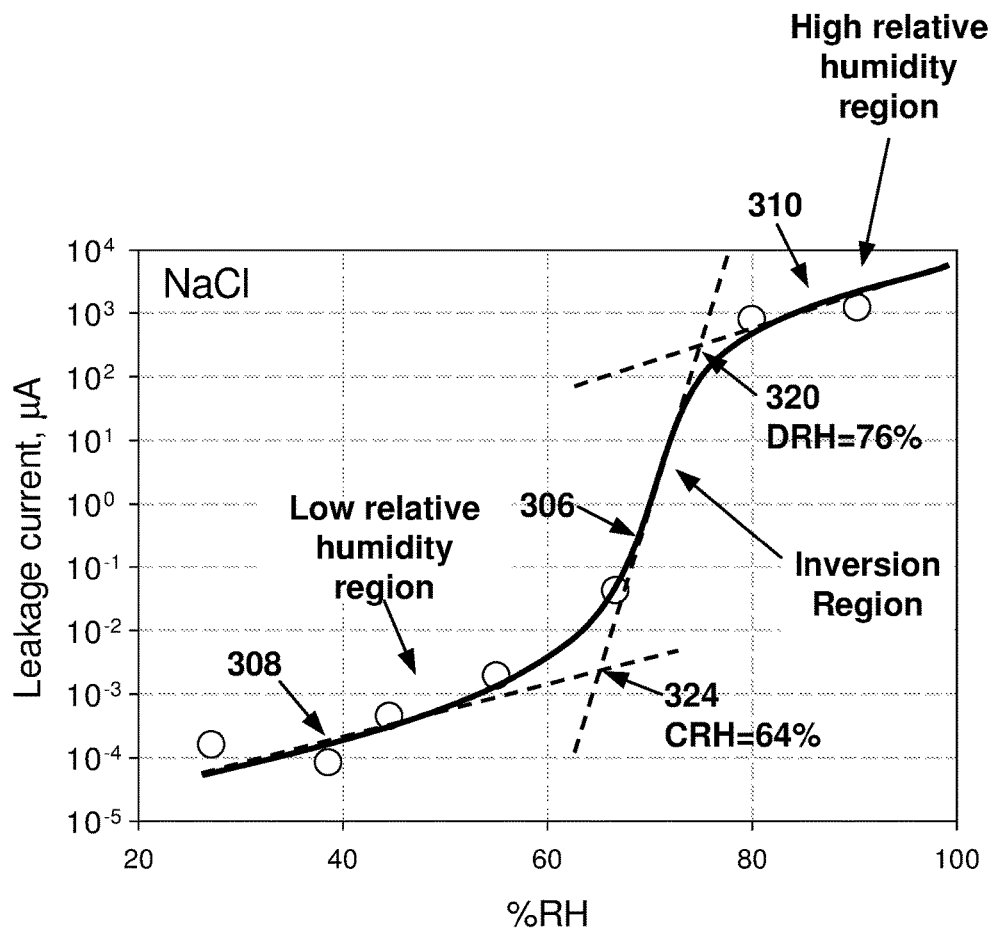

Referring now to FIG. 3, leakage current vs. percent relative humidity plots of different salts on a silver-plated interdigitated comb pattern at 25° C. using a logarithmic scale for the leakage current are shown, according to an embodiment of the present disclosure. As may be observed, the curves in FIGS. 3A-3C exhibit an S shape that may be made piece-wise linear by drawing straight lines covering an inversion region, a low relative humidity region and a high relative humidity region of the leakage current vs. percent relative humidity plot.

A high humidity asymptote 310 in the high humidity region of the curve intersects an inversion line 306 in the inversion region, and the intercept occurs at values very close to the published DRH values for the studied salts as may be observed. The physical origin of the S shape of the log (current leakage) versus percent relative humidity may be explained as follows: When the salt is in equilibrium with humidity in the low humidity range, a small increase in relative humidity does not change the salt's electrical conductivity significantly because the salt stays relatively dry. When the salt absorbs enough moisture to start approaching the deliquescence state, there is a rapid rise in conductivity resulting in the high slope of the inversion region of the curve. When the relative humidity rises above the DRH of the salt, the salt is fully dissolved and any further increase in humidity has little influence on the electrical conductivity of the salt solution. An intercept 320 between the high humidity asymptote 310 and the inversion line 306 may be considered to be the logical value for the DRH of the salt because it may refer to the relative humidity where the salt has absorbed just enough moisture to become wet enough that any further absorption of water will not increase its conductivity appreciably.

Another point of interest on the plots of FIGS. 3A-3C may be an intercept 324 between the inversion line 306 and the low humidity asymptote 308, which may be referred to as the critical relative humidity (CRH). The CRH is the point on the plot where the leakage current starts rising sharply as the relative humidity is raised. It may be prudent to keep the data center humidity below the CRH of the particulate matter to ensure that the accumulated particulate matter will not deteriorate the reliability of the IT equipment via electrical current leakages between closely spaced features on PCBs.

Additional experiments were conducted to study the effect of the square waveform voltage on the resulting DRH value derived from the leakage current at 0.01, 0.1, 1.0 and 10 V. Results have shown that voltage in the 0.01 to 10 V range may have no apparent effect on the leakage curves and the measured DRH and CRH values. It should be noted that this may apply to interdigitated comb coupons made of metals such as silver that do not oxidize. In the absence of surface oxides, the technique may work at voltages as low as 0.01 V. Interdigitated combs (e.g. interdigitated combs 102) made of tin plating may require higher voltages, approximately 10V, to break through the non-conductive tin oxide that forms readily on tin.

Similarly, the effect of metal plating on the interdigitated combs 102 was also studied. The study was conducted after changes in Restriction of Hazardous Substances (RoHS) regulations questioned the use of combs plated with other metals such as tin. Lead-free solders containing more than 95% tin currently form the majority of the metallization on PCBs. Experimental results were in agreement with published DRH values for the studied salts. However, if tin-plated comb patterns are used, the measurement voltage may need to be higher (~10 V) to overcome the effect of oxide cover on the tin plating.

To further test the validity of the proposed electrical method for measuring DRH of particulate matter, water uptake of $Mg(NO_3)_2$, $NH_4NO_3$ and NaCl was investigated using a gravimetric method. Results showed an excellent agreement between the gravimetric water uptake and the electrical leakage current measurements described above.

Figure 4:
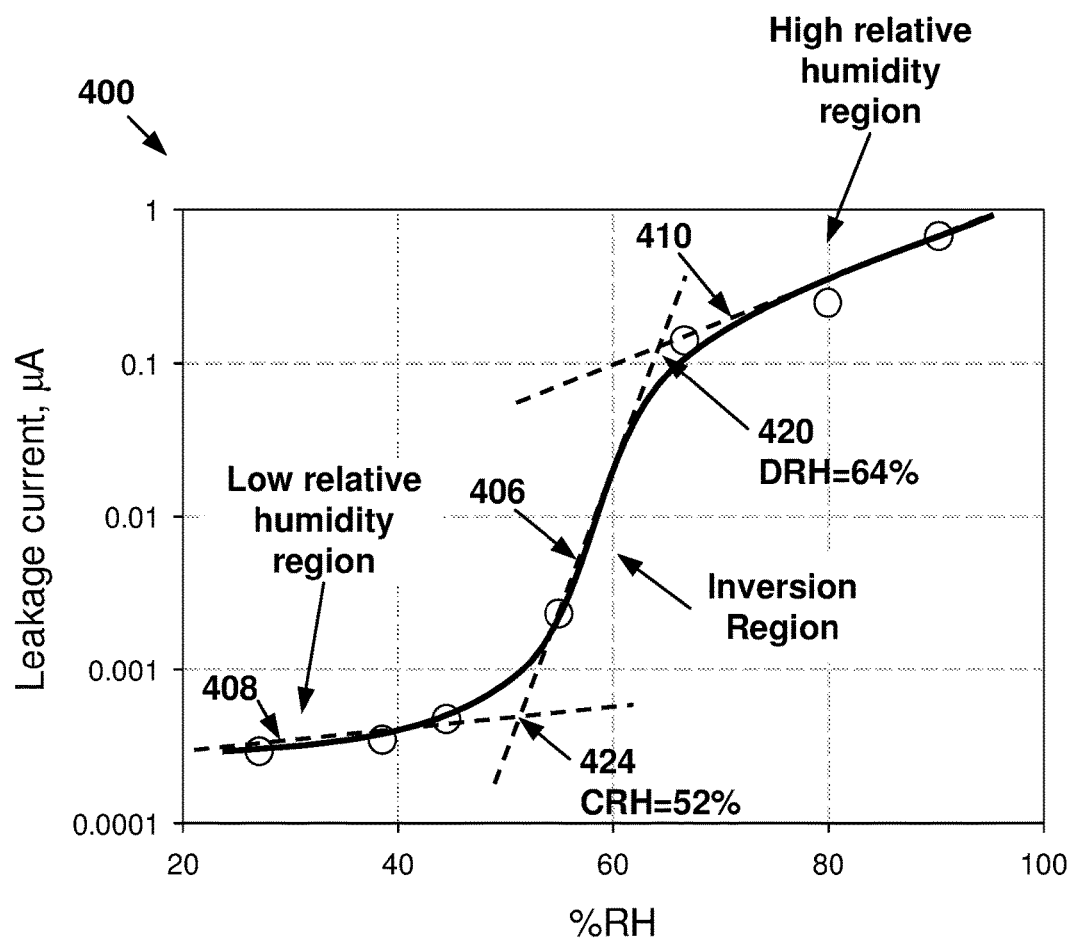
FIG. 4 depicts an exemplary plot of leakage current versus percent relative humidity at 30° C. for particulate matter that caused power supplies to fail in a data center location, according to an embodiment of the present disclosure.

Referring now to FIG. 4, an exemplary plot 400 of leakage current versus percent relative humidity at 30° C. for particulate matter that caused power supplies to fail in a data center location is shown, according to an embodiment of the present disclosure. This embodiment may be described as a field failure case history. The electrical method described above for measuring DRH was applied as part of a failure analysis. A plurality of failed power supplies showed no defect when functionally tested in the laboratory which may be typical of particulate matter related field failures. The power supplies were fully functional in the laboratory, most probably, because the electrically shorting particulate matter dried and became dislodged from where it was shorting the circuitry.

Following the particulate matter collection method described above, dust samples were collected in the laboratory. More specifically, a couple of power supplies were washed with a deionized water and isopropyl alcohol solution and the wash concentrated by evaporation. Ten drops of the concentrate, each 10 µl in volume, were dispensed on an interdigitated comb pattern. Then, DRH measurements were performed following the previously described method as shown in FIG. 4.

In this embodiment, from the leakage current versus percent relative humidity plot 400, a first intercept 420 between a high humidity asymptote 410 and an inversion line 406 corresponds to a DRH of approximately 64% for the tested particulate matter, while a second intercept 424 between the inversion line 406 and the low humidity asymptote 408 corresponds to a CRH of approximately 52% for the same particulate matter sample.

It should be noted that the data center relative humidity may be typically higher than the obtained values of DRH and CRH, averaging 70%, which may explain the failure of the power supplies. Also, the low CRH and DRH of the particulate matter may be attributed to high concentrations of salts, predominantly magnesium chloride ($MgCl_2$), found in the humidifier water. The power supply failures may be eliminated by removing these salts from the humidifier water using reverse osmosis.

Therefore, by applying the proposed method for DRH measuring, the relative humidity in the data center may be adjusted in order to prevent electrical current leakages between closely spaced features which may cause power supply failures.

Figure 5:
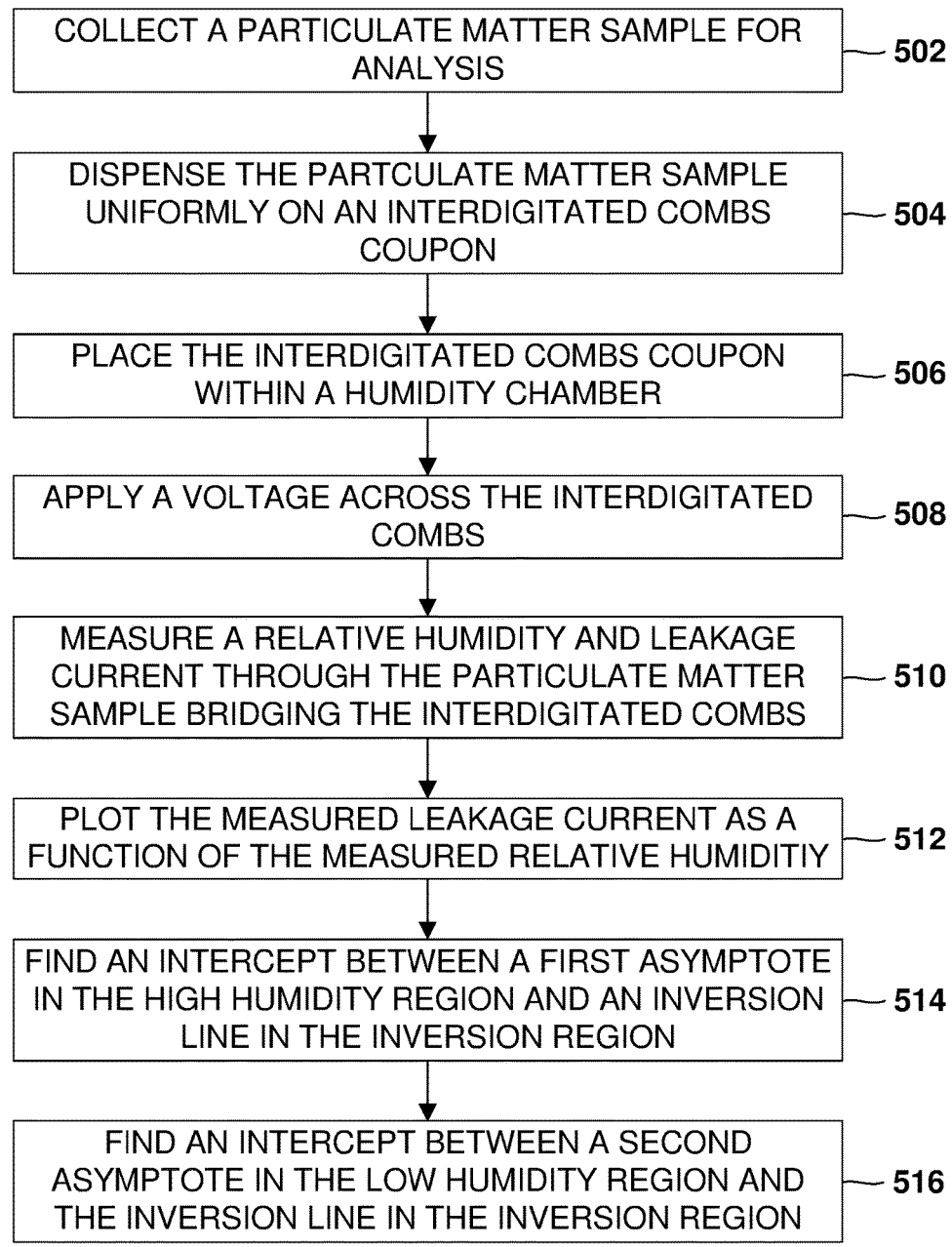
FIG. 5 depicts a flow chart describing the steps of a method for measuring deliquescence relative humidity of particulate matter, according to an embodiment of the present disclosure.

Referring now to FIG. 5, a flowchart 500 describing the steps of a method for measuring the deliquescence relative humidity of particulate matter is shown, according to an embodiment of the present disclosure. The proposed method may start at 502 by collecting a sample of particulate matter for analysis. The sample may be collected by any of the collection methods described above with reference to FIG. 1 and dispense uniformly at 504 on the interdigitated comb coupon 100 (FIG. 1). In a preferred embodiment, a contaminated circuit board may be provided and washed with a deionized water and isopropyl alcohol solution, the deionized water and isopropyl alcohol solution containing the particulate matter may be collected and evaporated to obtain a concentrated deionized water and isopropyl alcohol solution which may be dispensed on the interdigitated comb coupon 100 (FIG. 1) and dried.

The interdigitated comb coupon 100 (FIG. 1) may be placed at 506 within a humidity chamber in which a voltage may be applied at 508 across the plurality of interdigitated combs 102 (FIG. 1). The humidity in the chamber may be raised in steps of approximately 10% relative humidity and the leakage current measured at each humidity step using a +/−1 V square waveform. The relative humidity and a leakage current through the particulate matter sample bridging the plurality of interdigitated combs 102 (FIG. 1) in the interdigitated comb coupon 100 (FIG. 1) may be measured at 510. At 512 the logarithm of the measured leakage current may be plotted as a function of the measured relative humidity. As described above, when the logarithm of the leakage current is plotted against the measured relative humidity, an S shaped curve may be obtained having an inversion region, a low relative humidity region and a high relative humidity region.

At 514, from the plot of leakage current versus relative humidity (step 512), an intercept between a first asymptote in the high humidity region and an inversion line in the inversion region corresponds to the deliquescence relative humidity for the particulate matter sample. Additionally, at 516, an intercept between a second asymptote in the low humidity region and the inversion line in the inversion region corresponds to a critical relative humidity value for the same particulate matter sample.

By applying the described method, the deliquescence relative humidity and the critical relative humidity of particulate matter may be determined. As a result, particulate matter, including samples of 1 mg or less, may be tested to determine DRH and CRH values which may be used to adjust the data center environment such that particulate contamination may be prevented from entering the data center and settling on IT equipment. This may reduce failures associated with particulate matter contamination. Additionally, the method described may provide a way to clean contaminated equipment and collect particulate matter samples.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A method comprising:
providing a contaminated printed circuit board;
washing the contaminated printed circuit board with a deionized water and isopropyl alcohol solution;
collecting the deionized water and isopropyl alcohol solution containing the matter;
concentrating the deionized water and isopropyl alcohol solution by evaporation;
dispensing approximately 10 drops of 10 µl each of the concentrated deionized water and isopropyl alcohol solution on an interdigitated comb coupon to dry and form an uniform covering of particulate matter;

placing the interdigitated comb coupon comprising the uniform covering of particulate matter within a precision humidity chamber at a constant temperature;

measuring a relative humidity of, and a leakage current through, the particulate matter bridging a plurality of interdigitated combs, wherein an initial relative humidity in the precision humidity chamber comprises a lowermost value of a total capacity of the humidity chamber from which the relative humidity is raised in steps of 10% relative humidity of approximately one hour each, the leakage current is measured at each humidity step using a +/−1 V square waveform;

plotting a logarithm of the measured leakage current as a function of the measured relative humidity, wherein the plot of the logarithm of the measured leakage current as a function of the measured relative humidity comprises an S shaped curve having an inversion region, a low relative humidity region, and a high relative humidity region;

finding a first intercept between a first asymptote in the high humidity region and a second asymptote in the inversion region, wherein the first intercept comprises a deliquescence relative humidity of the particulate matter; and finding a second intercept between a third asymptote in the low humidity region and the second asymptote in the inversion region, wherein the second intercept comprises a critical relative humidity of the particulate matter sample.

* * * * *